United States Patent
Mothes et al.

(10) Patent No.: US 7,491,396 B2
(45) Date of Patent: Feb. 17, 2009

(54) PROCESS FOR THE PREPARATION OF HYPOALLERGENIC MOSAIC ANTIGENS

(75) Inventors: Nadine Mothes, Sollenau (AT); Sabine Stumvoll, St. Peter i.d.Au (AT); Margit Focke, Vienna (AT); Birgit Linhart, Weissenkirchen (AT); Maria-Theresa Krauth, Tribuswinkel (AT); Peter Valent, Vienna (AT); Dietrich Kraft, Vienna (AT); Rudolf Valenta, Theresienfeld (AT)

(73) Assignee: Biomay AG, Vienna (AT)

( * ) Notice: Subject to any disclaimer, the term of this patent is extended or adjusted under 35 U.S.C. 154(b) by 272 days.

(21) Appl. No.: 10/542,735

(22) PCT Filed: Dec. 18, 2003

(86) PCT No.: PCT/EP03/14507

§ 371 (c)(1),
(2), (4) Date: Jul. 21, 2005

(87) PCT Pub. No.: WO2004/065414

PCT Pub. Date: Aug. 5, 2004

(65) Prior Publication Data

US 2006/0263391 A1 Nov. 23, 2006

(30) Foreign Application Priority Data

Jan. 21, 2003 (EP) .................... 03001242

(51) Int. Cl.
*A61K 39/00* (2006.01)
*A61K 39/35* (2006.01)
*A61K 39/36* (2006.01)
*A61K 38/00* (2006.01)
*A01N 37/18* (2006.01)
*C07K 1/00* (2006.01)
*C07K 14/00* (2006.01)
*C07K 17/00* (2006.01)

(52) U.S. Cl. ............... 424/185.1; 424/275.1; 514/2; 530/350; 530/370

(58) Field of Classification Search .............. None
See application file for complete search history.

(56) References Cited

FOREIGN PATENT DOCUMENTS

EP 1 221 317 7/2002
WO WO 94/23035 3/1994

OTHER PUBLICATIONS

Rogers et al. 'Potential therapeutic recombinant proteins comprised of peptides containing recombined T cell epitopes.' Molecular Immunology 31(13):955-966.*
Kuby et al. 'Immunology.' Fourth Edicition, Chapter 18: 449-465.*
Mothes-Luksch et al. 'Disruption of allergenic activity of the major grass pollen allergen Phl p 2 by reassembly as a mosaic protein.' J. Immunol. 181(7):4864-4873, 2008.*
Valenta, R. et al., Immunol. Reviews, vol. 179, Feb. 2001, p. 119-127.
Valenta, R. et al., Joint Congress of the British Society for Immunology and the Biochem. Society, Dec. 10, 1996 (abstract only).
Focke, M. et al., FASEB, vol. 19(11), Sep. 2001, p. 2042-2044).
Dolecek, C. et al., FEBS Letters, vol. 335(3), 1993, p. 299-304.
Ansari, A. et al., J. Biol. Chem., vol. 264(19), 1989, p. 11181-11185.
Friedhoff, L. et al., J. Allergy Clin. Immunol., vol. 78(8), Jul. 1986, p. 1190-1201.
van Hage-Hamsten, M. et al., J. Allergy Clin. Immunol., vol. 104(5), Nov. 1999, p. 969-977.
Vratala, S. et al., J. Clin. Investigation, vol. 99(7), 1997, p. 1673-1681.
De Marino, S. et al., Structure, vol. 7(8), Aug. 1999, p. 943-952.
Akdis, C. et al., Int. Arch. Allergy Immunol., vol. 121(4), 2000, p. 261-269.
Ferreira, F. et al., Int. Arch. Allergy Immunol., vol. 128(3), Jul. 2002, p. 171-178.
Schramm, G. et al., J. Immunol., vol. 162(4), Feb. 1999, p. 2406-2414.

* cited by examiner

*Primary Examiner*—Maher M Haddad
*Assistant Examiner*—Nora M Rooney
(74) *Attorney, Agent, or Firm*—Chalin A. Smith; Smith Patent Consulting, LLC (57) ABSTRACT

A process for the preparation of an hypoallergenic mosaic antigen derived from an allergen is disclosed whereby a) in a first step the allergen is split into at least two parts and the IgE reactivity of each part is determined and b) in a second step those parts of the allergen which have no detectable IgE reaction are combined to a mosaic antigen which comprises the amino acids of the allergen but the order of the amino acids of the mosaic antigen is different from that of the naturally occurring allergen.

2 Claims, 12 Drawing Sheets

P2M-Sequence

```
ATG GTC CCG AAG GTG ACG TTC ACG GTG GAG AAG GGG TCC AAC GAG AAG CAC    51
 M   V   P   K   V   T   F   T   V   E   K   G   S   N   E   K   H    17
CTG GCG GTG CTG GTG AAG TAC GAG GGG GAC ACC ATG GCG GAG GTG GAG CTC   102
 L   A   V   L   V   K   Y   E   G   D   T   M   A   E   V   E   L    34
TTC CGG TTC CTC ACC GAG AAG GGC ATG AAG AAC GTC TTC GAC GAC GTC GTC   153
 F   R   F   L   T   E   K   G   M   K   N   V   F   D   D   V   V    51
CCA GAG AAG TAC ACC ATT GGG GCC ACC TAC GCG CCA GAA GAG CGG GAG CAC   204
 P   E   K   Y   T   I   G   A   T   Y   A   P   E   E   R   E   H    68
GGC TCC GAC GAG TGG GTC GCC ATG ACC AAG GGG GAG GGC GTG TGG ACG       255
 G   S   D   E   W   V   A   M   T   K   G   E   G   V   W   T        85
TTC GAC AGC GAG GAG CCG CTC CAG GGG CCC TTC AAC CAC CAC CAC CAC       306
 F   D   S   E   E   P   L   Q   Q   G   P   F   N   H   H   H   H   102
CAC                                                                   309
 H                                                                    103
```

Table 1.

| | Position aa | Sequence | Number of aa | Molecular weight | Isoelectric point |
|---|---|---|---|---|---|
| Peptide 1 | 1-33 | V P K V T F T V E K G S N E K H L A V L V K Y E G D T M A E V E L C | 34 | 3765,02 | 4.87 |
| Peptide 3 | 65-96 | R E H G S D E W V A M T K G E G G V W T F D S E E P L Q G P F N C | 33 | 3696,8 | 4.03 |
| Peptide 2 | 34-64 | C F R F L T E K G M K N V F D D V V P E K Y T I G A T Y A P E E | 32 | 3698,91 | 4.45 |

Table 2.

Induction of immediate skin reactions with Phl p 2 and Phl p 2 mosaic

Individual 1

| | mean wheal diameter (mm) | |
|---|---|---|
| | P2 | P2M |
| 1 µg/ml | 9 | 0 |
| 2 µg/ml | 10 | 0 |
| 4 µg/ml | 11 | 0 |
| 8 µg/ml | 14 | 5 |
| 16 µg/ml | 10 | 4 |
| Timothy grass | 15 | |
| Histamine | 8 | |

Individual 2

| | mean wheal diameter (mm) | |
|---|---|---|
| | P2 | P2M |
| 1 µg/ml | 5 | 0 |
| 2 µg/ml | 5 | 0 |
| 4 µg/ml | 6 | 0 |
| 8 µg/ml | 7 | 0 |
| 16 µg/ml | 9 | 3 |
| Timothy grass | 10 | |
| Histamine | 8 | |

Table 3. Rabbit anti P2 mosaic and rabbit anti-rPhl p 2 antibodies inhibit IgE binding of grass pollen allergic patients to rPhl p 2

| Patient | % inhibition | |
|---|---|---|
| | anti-P2M | anti-rPhl p 2 |
| 1 | 39.54 | 76.93 |
| 2 | 9.25 | 63.97 |
| 3 | 23.20 | 52.91 |
| 4 | 14.38 | 40.86 |
| 5 | 18.27 | 38.97 |
| Mean | 20.93 | 54.73 |

SEQUENCE LISTING

<160> NUMBER OF SEQ ID NOS: 12

<210> SEQ ID NO 1
<211> LENGTH: 103
<212> TYPE: PRT
<213> ORGANISM: artificial sequence
<220> FEATURE:
<223> OTHER INFORMATION: synthetic peptide

<400> SEQUENCE: 1

Met Val Pro Lys Val Thr Phe Thr Val Glu Lys Gly Ser Asn Glu Lys
1               5                   10                  15

His Leu Ala Val Leu Val Lys Tyr Glu Gly Asp Thr Met Ala Glu Val
            20                  25                  30

Glu Leu Phe Arg Phe Leu Thr Glu Lys Gly Met Lys Asn Val Phe Asp
        35                  40                  45

Asp Val Pro Glu Lys Tyr Thr Ile Gly Ala Thr Tyr Ala Pro Glu
    50                  55                  60

Glu Arg Glu His Gly Ser Asp Glu Trp Val Ala Met Thr Lys Gly Glu
65                  70                  75                  80

Gly Gly Val Trp Thr Phe Asp Ser Glu Glu Pro Leu Gln Gly Pro Phe
                85                  90                  95

Asn His His His His His His
            100

<210> SEQ ID NO 2
<211> LENGTH: 309
<212> TYPE: DNA
<213> ORGANISM: artificial sequence
<220> FEATURE:
<223> OTHER INFORMATION: synthetic cDNA

<400> SEQUENCE: 2
atggtcccga aggtgacgtt cacggtggag aaggggtcca acgagaagca cctggcggtg      60
ctggtgaagt acgaggggga caccatggcg gaggtggagc tcttccggtt cctcaccgag     120
aagggcatga agaacgtctt cgacgacgtc gtcccagaga agtacaccat tggggccacc     180
tacgcgccag aagagcggga gcacggctcc gacgagtggg tcgccatgac caaggggag     240 ggcggcgtgt ggacgttcga cagcgaggag ccgctccagg ggcccttcaa ccaccaccac     300
caccaccac                                                             309

<210> SEQ ID NO 3
<211> LENGTH: 34
<212> TYPE: PRT
<213> ORGANISM: artificial sequence
<220> FEATURE:
<223> OTHER INFORMATION: synthetic peptide

<400> SEQUENCE: 3

Val Pro Lys Val Thr Phe Thr Val Glu Lys Gly Ser Asn Glu Lys His
1               5                   10                  15

Leu Ala Val Leu Val Lys Tyr Glu Gly Asp Thr Met Ala Glu Val Glu
            20                  25                  30

Leu Cys

<210> SEQ ID NO 4
<211> LENGTH: 33
<212> TYPE: PRT
<213> ORGANISM: artificial sequence
<220> FEATURE:
<223> OTHER INFORMATION: synthetic peptide

<400> SEQUENCE: 4

Arg Glu His Gly Ser Asp Glu Trp Val Ala Met Thr Lys Gly Glu Gly
1               5                   10                  15

Gly Val Trp Thr Phe Asp Ser Glu Glu Pro Leu Gln Gly Pro Phe Asn
            20                  25                  30

Cys

<210> SEQ ID NO 5
<211> LENGTH: 32
<212> TYPE: PRT
<213> ORGANISM: artificial sequence
<220> FEATURE:
<223> OTHER INFORMATION: synthetic peptide

<400> SEQUENCE: 5

Cys Phe Arg Phe Leu Thr Glu Lys Gly Met Lys Asn Val Phe Asp Asp
1               5                   10                  15

Val Val Pro Glu Lys Tyr Thr Ile Gly Ala Thr Tyr Ala Pro Glu Glu
            20                  25                  30

<210> SEQ ID NO 6
<211> LENGTH: 34
<212> TYPE: DNA
<213> ORGANISM: artificial sequence
<220> FEATURE:
<223> OTHER INFORMATION: primer

<400> SEQUENCE: 6
ggatttccat atggtcccga aggtgacgtt cacg                          34

<210> SEQ ID NO 7
<211> LENGTH: 36
<212> TYPE: DNA
<213> ORGANISM: artificial sequence
<220> FEATURE:
<223> OTHER INFORMATION: primer

<400> SEQUENCE: 7
ggtgaggaac cggaagagct ccacctccgc catggt                        36

<210> SEQ ID NO 8
<211> LENGTH: 36
<212> TYPE: DNA
<213> ORGANISM: artificial sequence
<220> FEATURE:
<223> OTHER INFORMATION: primer

<400> SEQUENCE: 8

-continued

```
gcggaggtgg agctcttccg gttcctcacc gagaag                    36
```

<210> SEQ ID NO 9
<211> LENGTH: 36
<212> TYPE: DNA
<213> ORGANISM: artificial sequence
<220> FEATURE:
<223> OTHER INFORMATION: primer

<400> SEQUENCE: 9

```
ggagccgtgc tcccgctctt ctggcgcgta ggtggc                    36
```

<210> SEQ ID NO 10
<211> LENGTH: 36
<212> TYPE: DNA
<213> ORGANISM: artificial sequence
<220> FEATURE:
<223> OTHER INFORMATION: primer

<400> SEQUENCE: 10

```
tacgcgccag aagagcggga gcacggctcc gacgag                    36
```

<210> SEQ ID NO 11
<211> LENGTH: 51
<212> TYPE: DNA
<213> ORGANISM: artificial sequence
<220> FEATURE:
<223> OTHER INFORMATION: primer

<400> SEQUENCE: 11

```
cgcgaattct cagtggtggt ggtggtggtg gttgaagggc ccctggagcg g    51
```

<210> SEQ ID NO 12
<211> LENGTH: 51
<212> TYPE: DNA
<213> ORGANISM: artificial sequence
<220> FEATURE:
<223> OTHER INFORMATION: primer

<400> SEQUENCE: 12

```
cgcgaattct cagtggtggt ggtggtggtg ctcttctggc gcgtaggtgg c    51
```

PROCESS FOR THE PREPARATION OF HYPOALLERGENIC MOSAIC ANTIGENS

This application claims priority to European Patent Application No. 03.001242.1 filed Jan. 31, 2003, the contents of which are incorporated by reference herein in its entirety.

The present invention relates to mosaic antigens derived from naturally occurring allergens, in particular timothy grass pollen allergen Phl p 2. The mosaic antigens display reduced allergenic activity and are useful as allergy vaccines for the treatment of sensitized allergic patients and for prophylactic vaccination.

A large percentage of the population suffers from IgE-mediated allergies. Those patients suffer from allergic reactions against several antigens. A high percentage of the allergic reactions are caused by plant pollen. The symptoms of allergy like allergic rhinoconjunctivitis, asthma, dermatitis and even anaphylactic shock are due to IgE recognition of allergens. The IgE molecules are largely responsible for the symptoms of allergic reactions such as hay fever, asthma and hives.

The IgE molecules bind to an allergen like e.g. plant pollen. The tail region of the IgE molecule, the Fc part binds to Fc receptors which are mainly located on the surface of mast cells in tissues and basophils in the blood. Antigen binding triggers the mast cells or basophils to secrete a variety of cytokines and biologically active compounds, especially histamine. These molecules cause blood vessels to dilate and become leaky which in turn helps white blood cells, antibodies and complements components to enter sites of reaction. Those molecules are on the other hand largely responsible for the symptoms of allergic reactions. There are different degrees of allergic reactions which range from slight itching of the eyes and the symptoms of a slight cold over severe pains to live-threatening symptoms like anaphylactic shock which may occur for example after the sting of a bee.

In order to avoid these allergic reactions allergy vaccines have been developed which are based on the application of small amounts of hypoallergenic compounds. It is believed that by applying hypoallergenic vaccines IgG antibodies are produced which react with the allergen immediately after the individual has come into contact with the allergen. By those so-called blocking antibodies a contact between the allergen and the IgE molecules present in the patient's body is largely avoided. Therefore the reaction between the allergen and the mast cells mediated by IgE molecules is largely avoided.

In the field of therapy of allergic reactions different vaccines have been used. Formerly small amounts of the allergen have been applied to the patients. With the development of genetic engineering recombinant allergens may be used for vaccination. A major disadvantage of such allergen-containing vaccines is that the application of such vaccines causes in the patient unwanted side-effects. If for example the allergen against which the patient is allergic is applied subcutaneously to the patient an unwanted side-effect like itching up to anaphylatic shock can occur since the IgE antibodies present in the patient's body react with the allergen and cause the allergic reaction.

In order to overcome the undesired side-effects a process for the preparation of an hypoallergenic mosaic antigen derived from an allergen is disclosed whereby a) in a first step the allergen is split into at least two parts and the IgE reactivity of each part is determined and b) in a second step those parts of the allergen which have no detectable IgE reaction are combined to a mosaic antigen which comprises the amino acids of the allergen but the order of the amino acids of the mosaic antigen is different from that of the naturally occurring allergen.

The term "hypoallergenic mosaic antigen" provided by the present process means that the antigen comprises substantially all amino acids of the naturally occurring allergen. The difference compared with the naturally occurring antigen is, however, that the allergen is in a first step split into different parts. When the amino acid sequence of the allergen is known it is common general knowledge of a person skilled in the art to prepare peptides of varying lengths from the antigen. The peptides may either be prepared by chemical synthesis which is well-known in the art. Alternatively the peptides can be easily prepared by Polymerase Chain Reaction since suitable primers can be easily synthesized when the sequence is known.

The reactivity of each part of the allergen which is present as a peptide or polypeptide has to be determined. This can be done by reacting the peptide with sera from patients which are allergic against the naturally occurring allergen. The IgE antibodies present in such sera will react with the peptide if an IgE epitope is present on the peptide. If there are, however, no linear IgE epitopes or if conformational IgE epitopes are destroyed by separating the whole naturally occurring allergen there will be no binding of IgE with the peptide. The IgE antibodies can subsequently easily be detected by reaction with specific anti-antibodies which bind to the IgE antibody. Those anti-antibodies are usually labeled for detection.

It is an important aspect of the present invention to divide the allergen into such parts which do not react with IgE antibodies. If a part of the allergen still reacts with IgE antibodies in a substantial amount such parts of the allergen should not be used for the preparation of the mosaic antigen. It is advisable to test the parts of the naturally occurring antigen to be used in the mosaic antigen with sera from different allergic patients since there may be variations with regard to specifity and amount of IgE concentration in each serum.

When the allergen has been split up into several parts which do not have any detectable IgE reactivity those parts are newly arranged in order to provide the mosaic antigen. That the part of the allergen does not have a substantial IgE reactivity means that the IgE reactivity of the whole, naturally occurring allergen is tested with preferably at least five sera from allergic patients and the parts thereof are tested as well. The binding of IgE molecules to the allergen and the parts thereof is determined quantitatively and the IgE reactivity of the part has to be reduced to not more than 10%, preferably not more than 5% of the value obtained for the naturally occurring allergen.

The rearrangement of the parts of the naturally occurring allergen to the mosaic antigen means in the simplest case that the allergen is split up into two parts, namely part A having the N-terminus and ending at the cleavage side and part B starting with the cleavage side and ending with the carboxy terminus of the polypeptide. Cleavage site means the position in the polypeptide where one part ends and another part starts. If both parts of the naturally occurring antigen do not have a substantial IgE reactivity the two parts are rearranged in such a manner that now part B represents the N-terminus and part A represents the C-terminus.

When the naturally occurring allergen is split up into three parts having the naturally occurring order A, B and C there are several mosaic antigens possible, namely for example C, B, A; or A, C, B. The more parts are formed the more options for providing mosaic antigens are provided. In a preferred embodiment of the present invention it is avoided to combine parts which are localized in adjacent positions in the naturally occurring allergen, e.g. C, A, B. The reason therefore is that IgE binding epitopes may be formed again on the mosaic antigen. It is, however, essential that the mosaic antigen contains substantially all amino acids of the naturally occurring antigen. Certainly some amino acids which do clearly have no functions may be deleted or some amino acids may be deleted caused by production reasons, but as much as possible amino acids should be maintained. Moreover the mosaic antigen may also comprise amino acids used for production purposes. Preferably in the parts of the naturally occurring allergen which are reorganized in the mosaic antigen are as large as possible. The cleavage sites are preferably selected in order to destroy the IgE eptiopes whereby the IgE epitopes are maintained as far as possible.

In a preferred embodiment the process is used with allergens of group 2. Preferred group 2 allergens are described in the following publication:

Freidhoff L R, Ehrlich-Kautzky E, Grant J H, Meyers D A, Marsh D G. A study of the human immune response to *Lolium perenne* (rye) pollen and its components, Lol p I and Lol p II (rye I and rye II). I. Prevalence of reactivity to the allergens and correlations among skin test, IgE antibody, and IgG antibody data. J Allergy Clin Immunol 1986, 78, 1190-1201. Freidhoff L R, Ehrlich-Kautzky E, Meyers D A, Marsh D G. A study of the human immune response to *Lolium perenne* (rye) pollen and its components, Lol p I and Lol p II (Rye I and Rye II). II. Longitudinal variation of antibody levels in relation to symptomatology and pollen exposure and correction of seasonally elevated antibody levels to basal values. J Allergy Clin Immunol 1987, 80, 646-655. Ansari A A, Shenbagamurthi P, Marsh D G. Complete amino acid sequence of a *Lolium perenne* (perennial rye grass) pollen allergen, Lol p II. J Biol Chem 1989, 264, 11181-11185. Dolecek C, Vrtala S, Laffer S, Steinberger P, Kraft D, Scheiner O, Valenta R. Molecular characterization of Phl p II, a major timothy grass (*Phleum pratense*) pollen allergen. FEBS Lett 1993, 335, 299-304.

Figure 8:
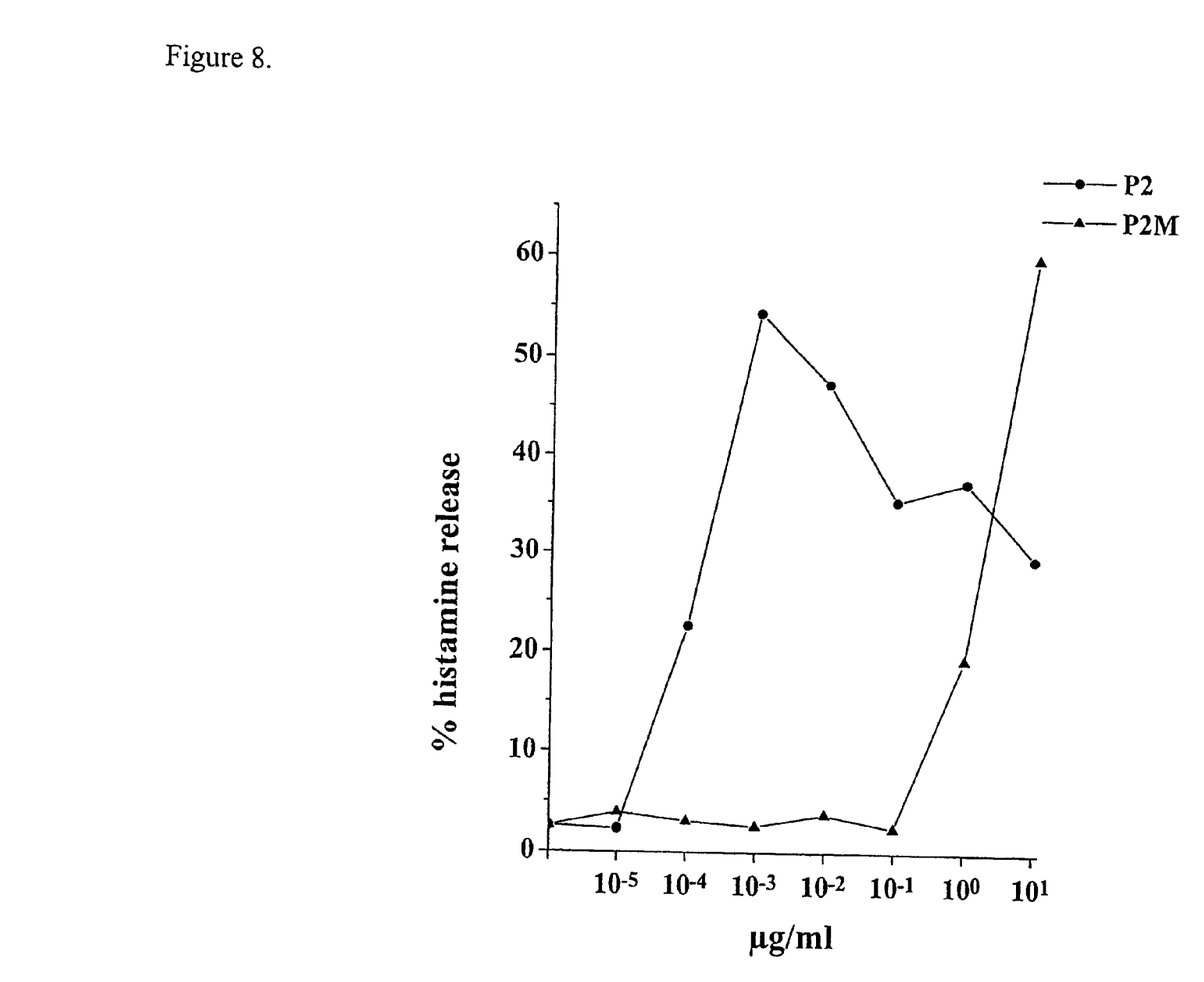

In an especially preferred embodiment the allergen used for the mosaic antigen is the timothy grass pollen allergen Phl p 2. The sequence of the grass pollen allergen Phl p 2 is disclosed in WO 94/23035. A more detailed description of the Phl p 2 from timothy grass pollen is provided in De Marino et al., Structure (1999) Vol. 7, No. 8, p. 943-952. The Phl p 2 antigen is preferred since it reacts with serum IgE from about 70% of grass pollen allergic individuals and elicits histamine release from basophils of sensitized patients.

In the course of the present invention it has been found that the Phl p 2 allergen is preferably split into three peptides, namely peptide 1 having amino acids 1-33, peptide 2 having amino acids 34-64 and peptide 3 having amino acids 65-96. By rearranging the peptides in the order 1, 3 and 2 a mosaic antigen is provided which can be used for hypoallergenic vaccination. This mosaic antigen has the advantage that a sufficient amount of blocking IgE antibodies is produced, but the undesired side-reactions associated with the vaccination are nearly completely avoided.

The amino acid sequence of the preferred mosaic allergen has SEQ ID NO:1. The DNA coding for this preferred mosaic allergen has SEQ ID NO:2.

The mosaic allergen provided by the present disclosure can preferably be used for the preparation of a medicament for the treatment of an allergic reaction. The preferred Phl p 2 mosaic antigen can be used for the preparation of a medicament for the treatment of grass pollen allergy. Since the Phl p 2 is an antigen against which a large percentage of allergic patients have formed IgE antibodies the mosaic antigen is very helpful in the treatment of patients suffering from hay fever.

A mosaic antigen as prepared by the described process can be formulated as a medicament for the treatment of an allergic reaction. The main component is the mosaic antigen which is preferably administered together with an adjuvant. There are several adjuvants which are suitable for the application to humans like e.g. aluminium hydroxide gel. In another embodiment of the present invention it is also possible to link the mosaic antigen directly by covalent binding to another component which generally enhances the immunologic reaction of the body.

It is also possible to use a DNA coding for a mosaic antigen or a DNA sequence complementary thereto as a DNA vaccine. For nucleic acid vaccines a suitable polynucleotide sequence is inserted into the target cells. In addition to the sequence coding for the mosaic antigen such a DNA vaccine may also contain regulatory elements like promoters, ribosome bindinig sites or termination sequences. Such DNA sequences should preferably be incorporated into a suitable carrier which allows the DNA to come to the protein synthesizing machinery of the cells.

A mosaic antigen as described in detail herein is preferably intended for human application. It is, however, also possible to use the mosaic antigen for valuable animals like pets (e.g. dogs or cats) or horses.

The figures and tables describe preferred embodiments of the present invention:

FIG. 1: Comparison of the IgE reactivity of synthetic Phl p 2-derived peptides and complete rPhl p 2 (recombinantly produced wild type allergen). Nitrocelluloses containing (A) dotted Phl p 2 peptides (P1, P2, P3), human serum albumin (HSA), a control peptide (P), and a non-cross-reactive timothy grass pollen allergen (rPhl p 5) and (B) rPhl p 5 and Phl p 2 (rPhl p 2) were exposed to sera from 35 grass pollen allergic patients (1-35) and to serum from a non-allergic individual (N).

FIG. 2: Schematic representation of recombinant his-tagged Phl p 2 wildtype and recombinant his-tagged Phl p 2 mosaic. The position of the three peptides is indicated.

FIG. 3: DNA sequence of the primers used for the construction of the Phl p 2 mosaic and schematic representation of PCR approach used for the assembly of the cDNA coding for the rPhl p 2 mosaic. The Nde I and Eco R I restriction sites are underlined in primer P2/1 and P2/6, respectively. The primers correspond to SEQ ID NO:6 to SEQ ID NO:11.

FIG. 4: cDNA (SEQ ID NO:2) and deduced amino acid sequence (SEQ ID NO:1) and of the his-tagged Phl p 2 mosaic. Aminoacids are displayed in the single letter code, base pair and amino acid numbers are shown on the right margin.

FIG. 5: Purity of rPhl p 2 mosaic and rPhl p 2. Comassie stained gel containing Phl p 2 (lane P2), Phl p 2 mosaic (lane P2M) and a molecular weight marker (lane M).

FIG. 6: Mass spectroscopical analysis of purified rPhl p 2 mosaic (A) and rPhl p 2 (B). The mass/charge ratio is shown on the x-axis and the signal intensity is expressed as percentage of the most intensive signal obtained in the investigated mass range.

FIG. 7: Comparison of the IgE binding capacity of rPhl p 2 (P2) and the rPhl p 2 mosaic (P2M). Nitrocellulose dotted rPhl p 2 (P2) and rPhl p 2 mosaic (P2M), as well as human serum albumine (HSA) were probed with serum from 12 Phl p 2-reactive grass pollen allergic patients (1-12). Bound IgE antibodies were detected with $^{125}$I-labeled anti-human IgE antibodies and visualized by autoradiography.

FIG. 8: Reduced allergenic activity of rPhl p 2 mosaic determined by basophil histamine release. Basophils from a grass pollen allergic patient were exposed to increasing concentrations of rPhl p 2 and rPhl p 2 mosaic (x-axis). Histamine release is expressed as percentage of total histamine release on the y-axis.

Table 1: Characteristics of Phl p 2-derived synthetic peptides. Sequence, number of amino acids, position in the Phl p 2 allergen; molecular weight and isoelectric point of the peptides are displayed. Peptide 1 corresponds to SEQ ID NO:3, Peptide 3 corresponds to SEQ ID NO:4 and Peptide 2 corresponds to SEQ ID NO:5.

Table 2: Immediate type skin reactions to complete rPhl p 2 and to Phl p 2 mosaic (P2M). Two timothy grass pollen allergic patients (Individual 1,2) were tested for skin reactivity with P2 and P2M. The mean wheal diameters (mm) are displayed for five different concentrations of rPhl p 2 and Phl p 2 mosaic, as well as for timothy grass pollen extract and histamine.

Table 3: Inhibition of grass pollen allergic patients IgE binding to rPhl p 2 by rabbit αP2M and rabbit αP2 antibodies. The percentage inhibition of IgE binding is displayed for 5 patients.

The invention is further illustrated by the following examples:

EXAMPLE 1

Synthetic Phl p 2-derived Peptides Lacking Allergenic Activity

In order to identify Phl p 2 fragments without allergenic activity, peptides, each comprising about ⅓ of the Phl p 2 protein were chemically synthesized (Table 1). The peptides had a length between 32 and 34 aminoacids with molecular weights of around 3.7 kDa and together covered the complete Phl p 2 amino acid sequence.

The three peptides were synthesized using Fmoc (9-fluorenylmethoxycarbonyl)-strategy with HBTU (2-(1H-benzotriazol-1-yl) 1,1,3,3, tetramethyluronium hexafluorophosphat)-activation (0.1 mmol small-scale cycles) on the Applied Biosystems (Foster City, Calif.) peptide synthesizer Model 433A. Preloaded PEG-PS (polyethylenglycol polysterene) resins (0.15-0.2 mmol/g loading) (per Septive Biosystems, Warrington, UK) were used as solid phase to build up the peptides. Chemicals were purchased from Applied Biosystems. Coupling of amino acids was confirmed by conductivity monitoring in a feedback control system. One cysteine residue was added to each peptide at the N- or C-terminus to facilitate coupling of the peptides to carriers. Peptides were cleaved from the resins with a mixture of: 250 µl dest. water, 250 µl Triisopropylsilan (Flukan, Buchs, Switzerland), 9.5 ml TFA for 2 h and precipitated in tert-Butylmethylether (Flukan, Buchs, Switzerland). The identitiy of the peptides was checked by mass-spectrometry and they were purified to >90% purity by preparative HPLC (PiChem, Graz; Austria) (Focke M, Mahler V, Ball T,. Sperr. W R, Majlesi Y, Valent P, Kraft D, Valenta R. Nonanaphylactic synthetic peptides derived from B cell epitopes of the major grass pollen allergen, Phl p 1, for allergy vaccination. FASEB J. 2001, 15: 2042-2044.

Figure 1:
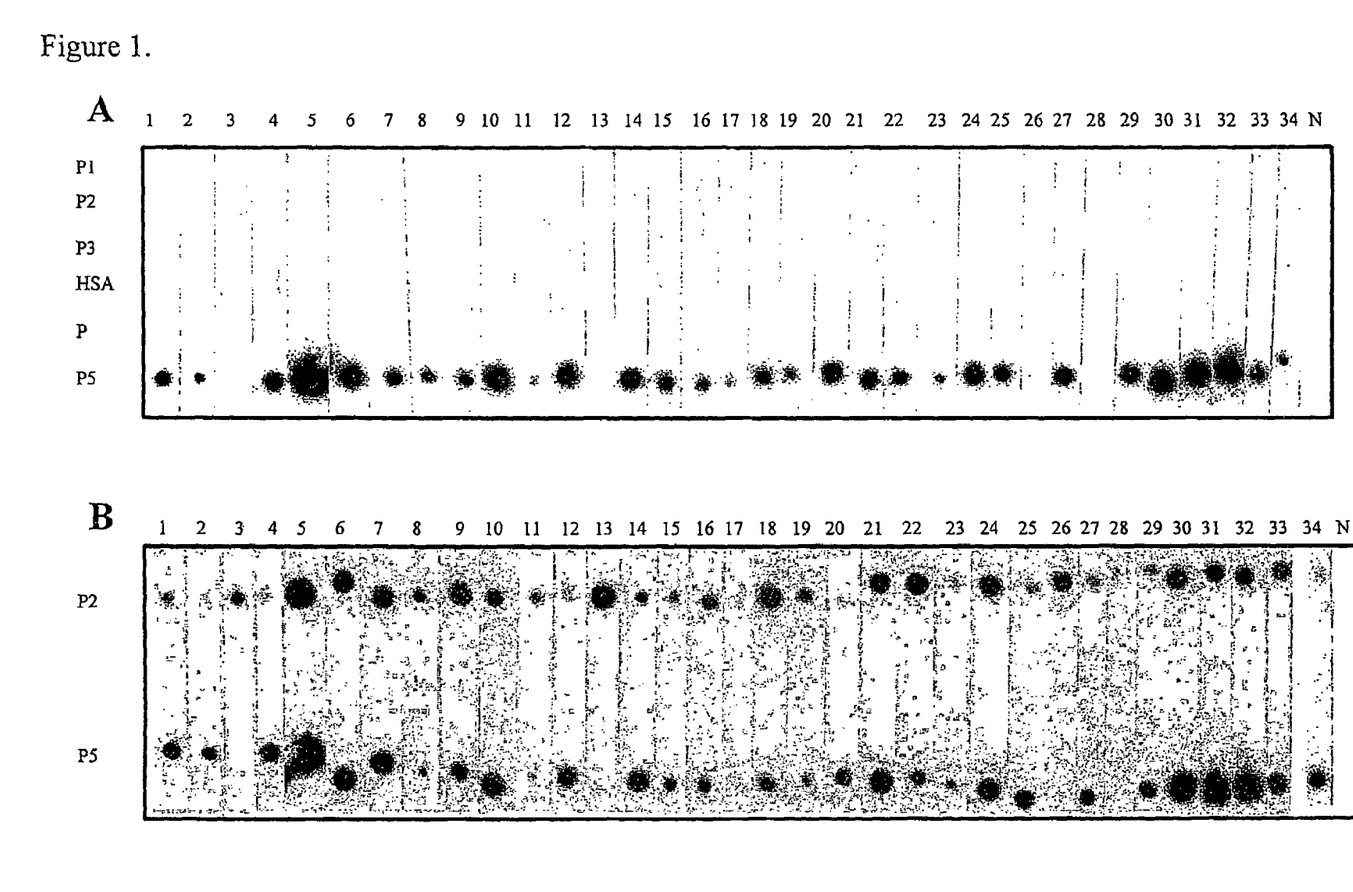
Figure 2:
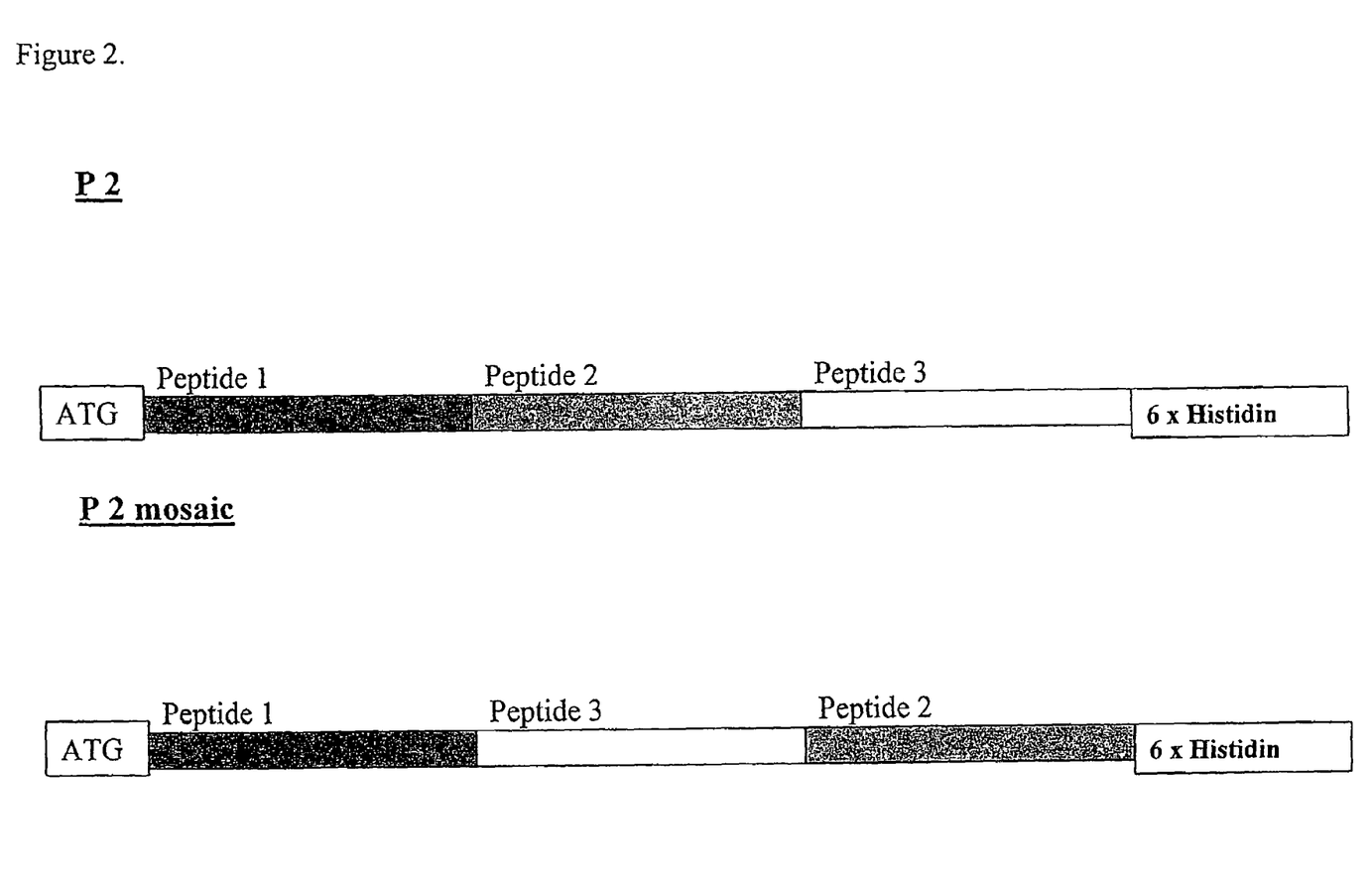
Figure 3:
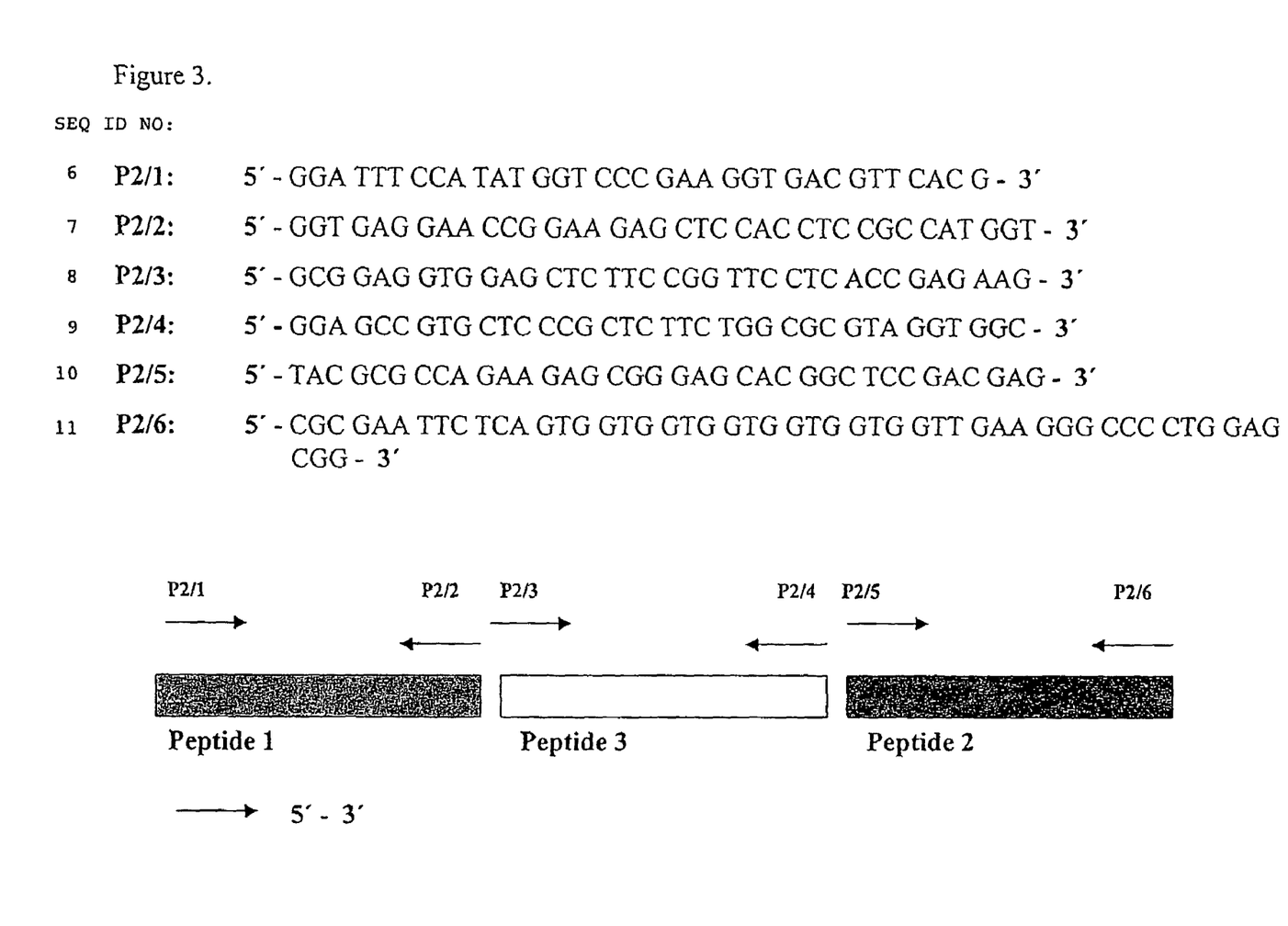

The allergenic activity of the Phl p 2-derived peptides was evaluated by comparing the IgE-reactivity of complete rPhl p 2 with the peptides by dot blot analysis (FIG. 1). Nitrocellulose-dotted Phl p 2-derived peptides (P1-P3), an immunologically unrelated major grass pollen allergen, rPhl p 5 (Vrtala S, Sperr W R, Reimitzer I, van Ree R, Laffer S, Müller WD, Valent P. Lechner K, Rumpold H, Kraft D, Scheiner O, Valenta R. cDNA cloning of a major allergen from timothy grass (*Phleum pratense*) pollen; characterization of the recombiniant Phl p V allergen. J. Immunol. 1993, 151: 4773-4781), and for control purposes, human serum albumin as well as a control peptide were exposed to sera from grass pollen allergic patients and to serum from a non-allergic individual.

Bound IgE antibodies were detected as described previously (Valenta R. Duchene M, Ebner C, Valent P, Sillaber C, Deviller P, Ferreira F, Tejkl M, Edelmann H, Kraft D, Scheiner O. Profilins constitute a novel family of functional plant pan-allergens. J. Exp. Med. 1992, 175: 377-385). Sera from all 35 grass pollen allergic patients showed IgE reactivity to nitrocellulose-dotted rPhl p 2 but no serum reacted with any of the three Phl p 2-derived peptides (FIG. 1). Serum from the non-allergic individual displayed no IgE reactivity to any of the peptides or proteins.

EXAMPLE 2

Characterization of the Recombinant Phl p 2 Mosaic Protein

A recombinant Phl p 2 mosaic protein was obtained by recombination of the three Phl p 2-derived peptides in altered sequence. This mosaic protein was created under the assumption that recombination of three non-allergenic Phl p 2 fragments in altered order will deliver a mosaic protein with disrupted three-dimensional structure and consequently reduced allergenic activity. In addition it was expected that the mosaic protein will exhibit better immunogenicity compared to the individual smaller peptide units and preserve the entire primary amino acid sequence of Phl p 2 thus containing the relevant T cell epitopes of Phl p 2.

FIG. 2 shows the assembly of the three peptides in the natural Phl p 2 allergen compared to that of the Phl p 2 mosaic protein. In order to compare the two proteins a recombinant Phl p 2 containing: a C-terminal hexahistidine tail and a recombinant Phl p 2 mosaic protein was produced which also contained a C-terminal hexahistidine tail (FIG. 2) to allow the purfication of both proteins by Nickel affinity chromatography (Quiagen, Hilden, Germany).

The recombinant Phl p 2 mosaic was construed by PCR-based gene amplification of cDNAs coding for the three peptides in the order shown in FIG. 2 using the primers displayed in FIG. 3 and the Phl p 2-encoding cDNA (Dolecek C, Vrtala S, Laffer S, Steinberger P, Kraft D, Scheiner O, Valenta R. Molecular characterization of Phl p II, a major timothy grass (*Phleum pratense*) pollen allergen. FEBS Lett. 1993, 335: 299-304) as template as described (Linhart B. Jahn-Schmid B, Verdino P, Keller W, Ebner C, Kraft D, Valenta R. Combination vaccines for the treatment of grass pollen allergy consisting of genetically engineered hybrid molecules with increased immunogenicity. FASEB J. 2002, 16: 1301-1303).

FIG. 4 shows the DNA and deduced amino acid sequence of the recombinant Phl p 2 mosaic protein. The his-tagged mosaic protein is encoded by a DNA of 309 bp coding for a protein with a calculated molecular of 11769 Da almost identical to the his-tagged recombinant Phl p 2 allergen (11784 Da).

The cDNA coding for a his-tagged rPhl p 2 allergen was obtained by PCR using a combination of the 5' primer P2/1 (SEQ ID NO:6) and the 3' primer P2/7 (SEQ ID NO:12): CGC GAA TTC TCA GTG GTG GTG GTG GTG GTG CTC TTC TGG CGC GTA GGT GGC and the cDNA coding for Phl p 2 as a template.

Figure 4:
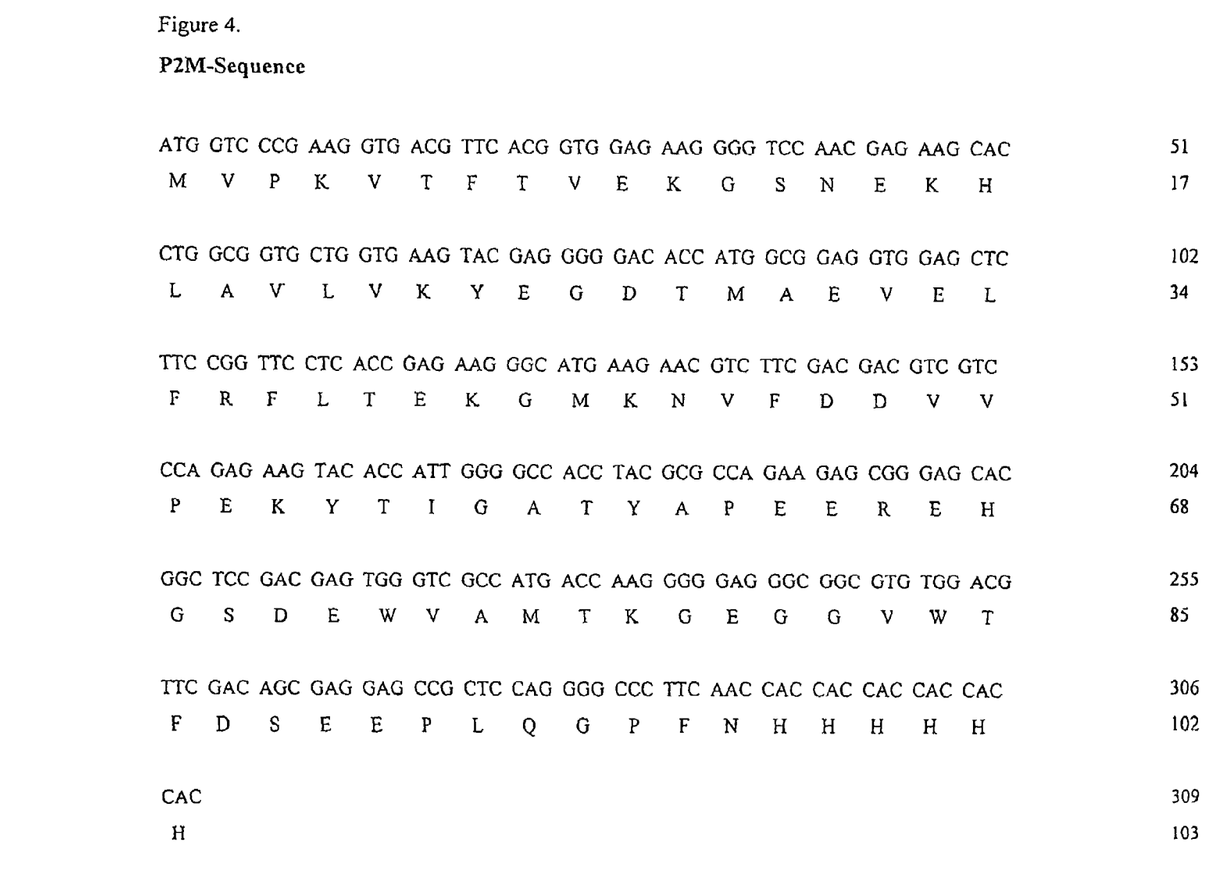

The cDNAs coding for the his-tagged Phl p 2 mosaic and the his-tagged Phl p 2 allergen were separately ligated into Nde I/Eco RI cut plasmids pET17b (Novagen). The DNA sequences of the two plasmid constructs was confirmed by sequence analysis and the recombinant proteins were expressed in *Escherichia coli* BL21 (DE3) (Novagen) by induction with 0.5-mM isopropyl-β-thiogalactopyranoside at an optical density at 600 nm of 0.4 in liquid culture (LB, medium containing 100 mg/l ampicillin) for additional 4 hours at 37° C. *E. coli* cells from a 500 ml culture were harvested by centrifugation and prepared for purificaton under native (rPhl p 2) or denaturing conditions (rPhl p 2 mosaic) according to the manufactorers advice (Quiagen, Hilden, Germany). Protein samples were analysed for purity by sodium dodecyl sulfate-polyacrylamide gel electrophoresis (SDS-PAGE) and protein staining (Fling S P, Gregerson D S. Peptide and protein molecular weight determination by electrophoresis using a high-molarity Tris buffer system without urea. Anal. Biochem. 1986, 155:83-88) (FIG. 4).

Figure 5:
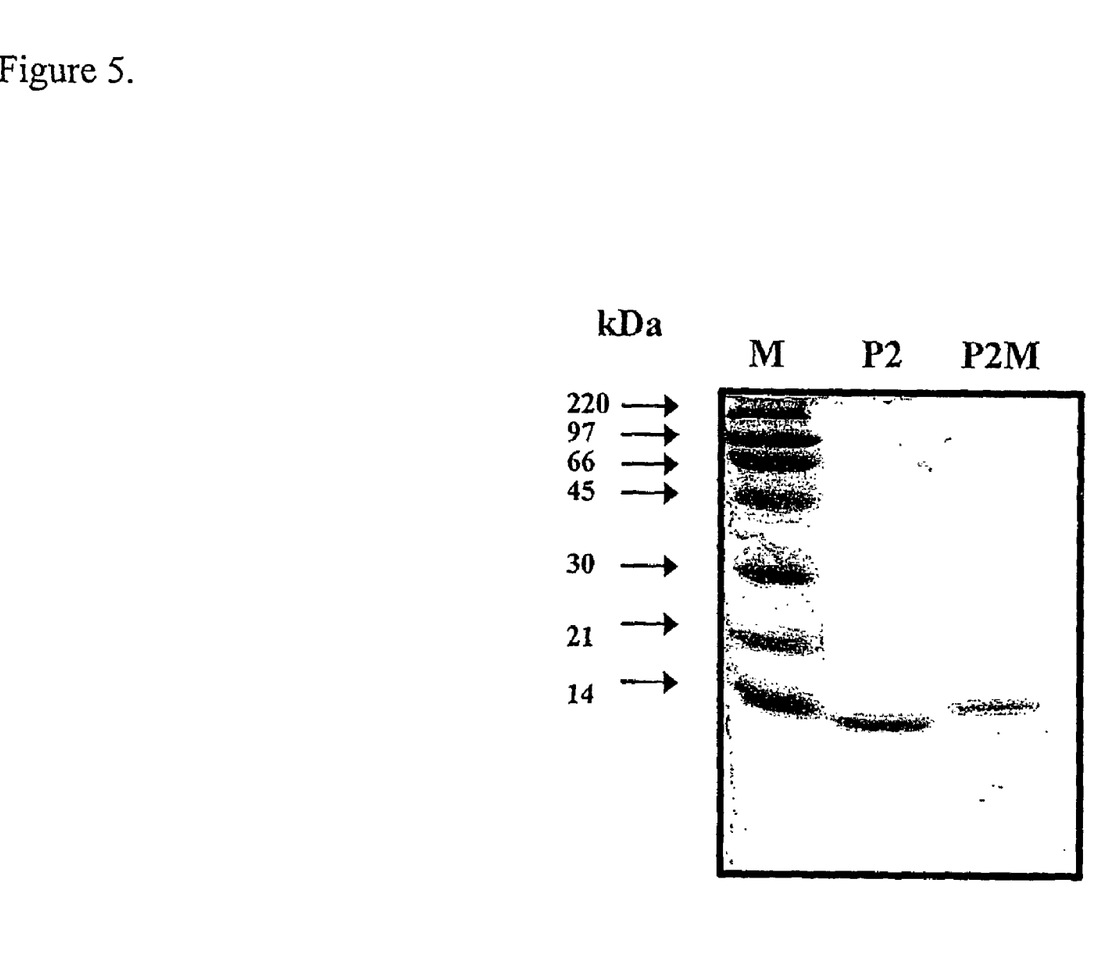
Figure 6:
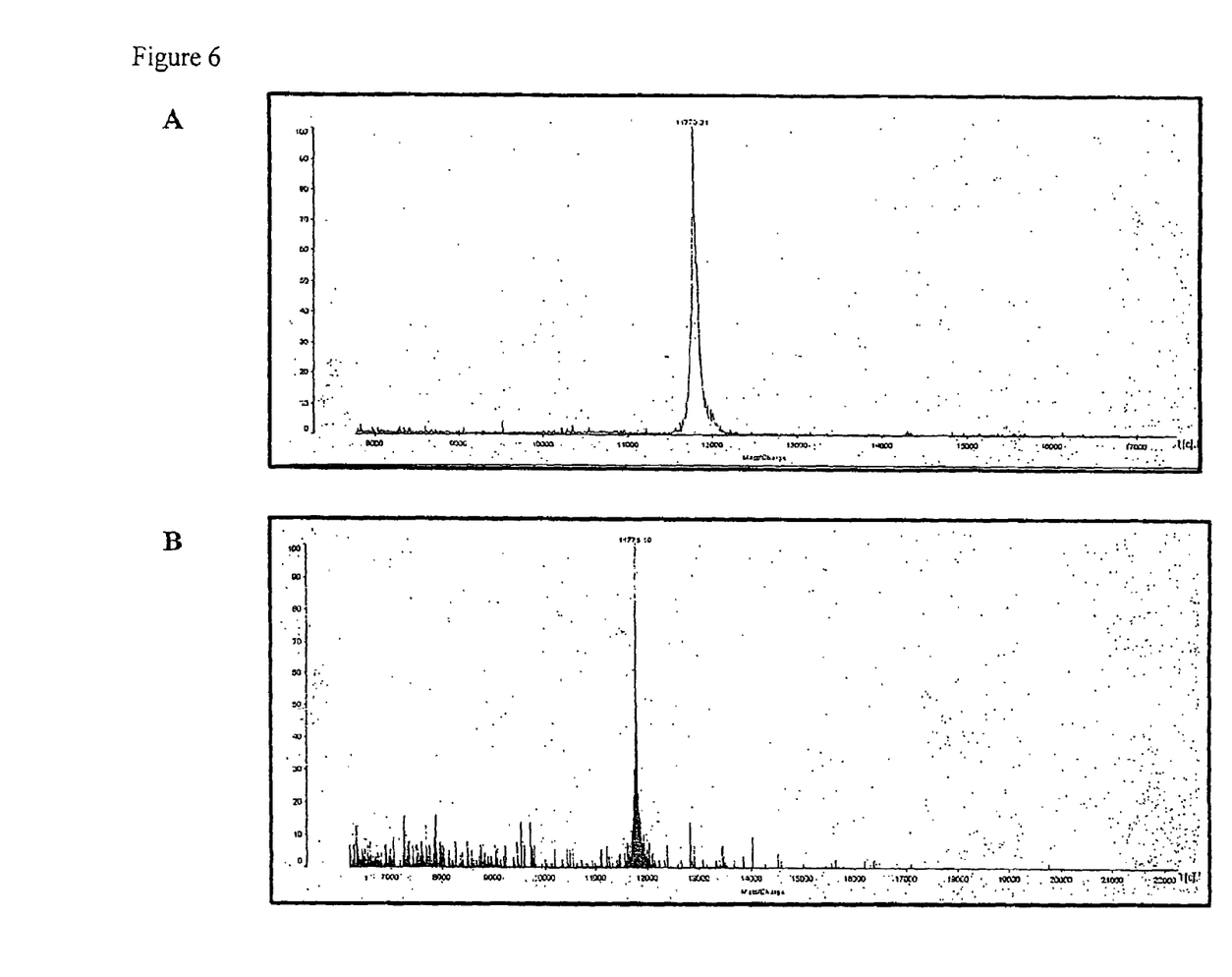

FIG. 5 shows the purity of the his-tagged recombinant proteins (rPhl p 2: P2; rPhl p 2 mosaic: P2M). Although the two proteins did not show a completely identical migration behaviour in the SDS-PAGE, mass spectroscopical analysis performed as described by Niederberger V, Hayek B, Vrtala S, Laffer S, Twardosz A, Vangelista L, Sperr W R, Valent P, Rumpold H, Kraft D, Ehrenberger K, Valenta R, Spitzauer S. Calcium-dependent immunoglobulin E recognition of the apo- and calcium-bound form of a cross-reactive two EF-hand timothy grass pollen allergen, Phl p 7. FASEB J. 1999, 13: 843-856 showed almost identical molecular weights of the two proteins (rPhl p 2: 11775 Da; rPhl p 2 mosaic: 11770 Da) which were in good agreement with the deduced molecular weights including the methionines at their N-terminus (FIG. 6).

EXAMPLE 3 rPhl p 2 Mosaic Lacks IgE Reactivity and Allergenic Properties

Figure 7:
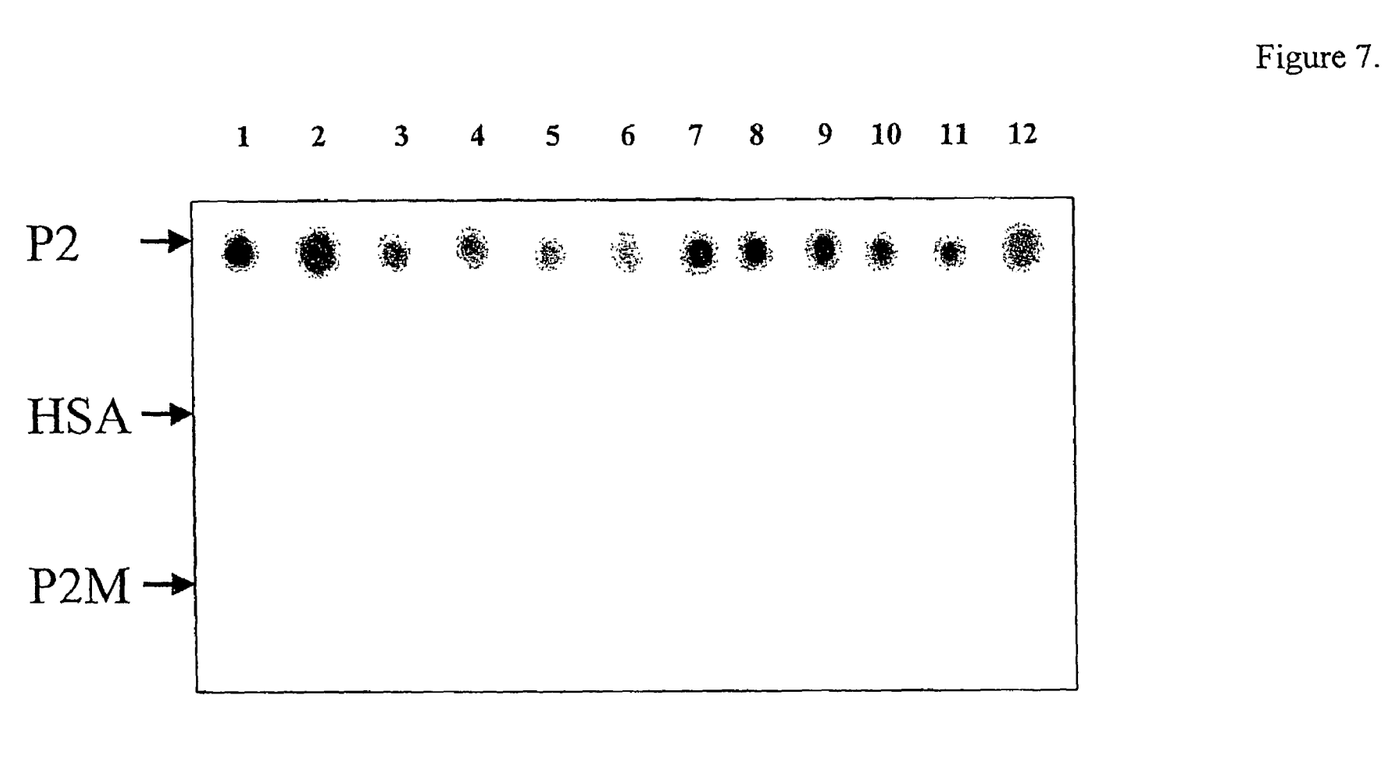

The IgE binding capacity of purified Phl p 2 mosaic (P2M) was compared with that of Phl p 2 wildtype by dot blot experiments as described for the peptides using sera from twelve timothy grass pollen allergic patients (FIG. 7). Sera from all 12 grass pollen allergic patients contained IgE antibodies against rPhl p 2 but no serum exhibited IgE reactivity to the rPhl p 2 mosaic or the negative control, human serum albumin (FIG. 7). The strongly reduced allergenic activity of the rPhl p 2 mosaic was further demonstrated by basophil histamine release and skin test experiments. Basophils from a grass pollen allergic patient were enriched by dextran sedimentation and exposed to increasing concentrations of purified rPhl p 2 or rPhl p 2 mosaic as described (Valent P, Besemer J, Muhm M, Majdic O; Lechner K, Bettelhei P. Interleukin 3 activates human blood basophils via high-affinity binding sites. Proc. Natl. Acad. Sci. USA 1989, 86: 5542-5546).

Histamine released in the cell free supernatants was determined in triplicates by radioimmuno assay and is expressed as mean percentage of the total histamine content of the cells as described by Valent et al.

FIG. 8 shows that the rPhl p 2 mosaic (maximal release between 1 and 10 μg/ml) exhibited a more than 1000 fold reduced allergenic activity compared to the rPhl p 2 allergen (maximal release $10^{-3}$ μg/ml).

The strongly reduced allergenic activity of rPhl p 2 mosaic was confirmed by skin testing in grass pollen allergic patients (Table 2). SPTs (skin prick tests) were performed on the individuals' forearms. Twenty microliter aliquots containing 5 concentrations of rPhl p 2 and of Phl p 2-derived mosaic P2M (1 μg/ml, 2 μg/ml, 4 μg/ml, 8 μg/ml, 16 μg/ml) were applied. In addition, standardized skin prick solutions (timothy grass pollen extract and histamine) (Allergopharma, Reinbeck, Germany) were tested. Reactions were recorded 20 minutes after SPT by photography and by transferring the ballpoint pen-surrounded wheal area with a scotch tape to paper. The mean wheal diameter (Dm) was calculated by measuring the maximal longitudinal and transversal diameter and dividing their sum by 2 as described by Focke et al., 2001.

rPhl p 2 induced strong wheal reactions already at the lowest concentration tested, i.e., 1 μg/ml, whereas rPhl p 2 mosaic induced only mild wheal reactions at the maximal concentrations tested (i.e., 8-16 μg/ml) thus confirming the reduced allergenic activity of the mosaic protein.

EXAMPLE 4

Immunization with the rPhl p 2 Mosaic Induces IgG Antibodies that Recognize rPhl p 2 Wildtype and Inhibit Allergic Patients IgE Binding to Phl p 2

In order to test whether immunization with Phl p 2 mosaic and Phl p 2 mosaic will induce IgG antibodies that react with natural Phl p 2, rabbits were immunized with rPhl p 2 mosaic, KLH-coupled rPhl p 2 mosaic or rPhl p 2 using Freund's adjuvant as described by Focke et al.

Figure 9:
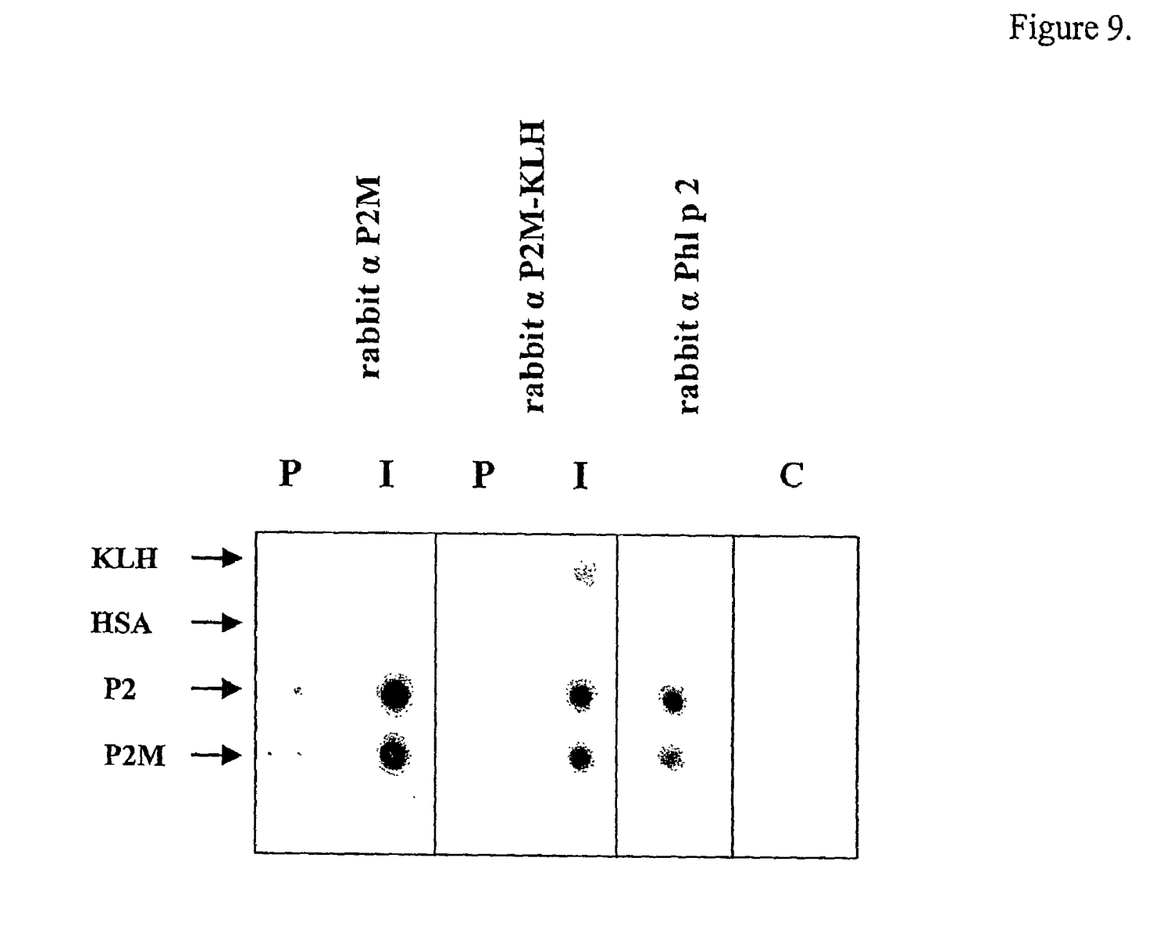
FIG. 9: Rabbit anti-rPhl p 2 mosaic antibodies recognize the rPhl p 2 wildtype allergen. Rabbit antisera raised against the rPhl p 2 mosaic (αP2M), KLH-coupled mosaic (αP2M-KLH) and rPhl p 2 (αPhl p 2) as well as buffer (C) were exposed to dot-blotted KLH, human serum albumin (HSA), rPhl p 2 (P2) and rPhl p 2 mosaic (P2M). Bound rabbit antibodies were detected with $^{125}$I-labeled donkey anti-rabbit IgG and visualized by autoradiography.

The reactivity of rabbit IgG antibodies with rPhl p 2 was studied by dot blot experiments (FIG. 9). Phl p 2 wildtype (P2) as well as the corresponding immunogen Phl p 2 mosaic (P2M) were dotted onto nitrocellulose-strips (1 μg/dot). Nitrocelluloses were exposed to the rabbits preimmune or immune sera (1:500) and bound rabbit antibodies were detected with a 1:1000 diluted $^{125}$I-labeled donkey anti-rabbit antiserum (Amersham Pharmacia Biotech) as described by Valenta et al., 1992.

The rabbit anti-rPhl p 2 mosaic antiserum reacted strongly with the immunogen (rPhl p 2 mosaic) as well as with the rPhl p 2 allergen (FIG. 9). The antibody reactivity was of comparable intensity as that obtained with the antiserum produced by immunization with the KLH-coupled mosaic and stronger than the reactivity induced by immunization with the rPhl p 2 allergen (FIG. 9).

EXAMPLE 6

Measurement of Blocking Antibodies

It was studied whether IgG antibodies induced by immunization with the rPhl p 2 mosaic inhibit the binding of allergic patients' serum IgE to complete rPhl p 2 by ELISA competition using sera from five grass pollen allergic patients (Table 3). ELISA plates (Nunc Maxisorp, Rokslide, Denmark) were coated with rPhl p 2 (1 μg/ml) and preincubated either with a 1:100 dilution of each of the anti-Phl p 2 mosaic and anti-Phl p 2 antiserum and, for control purposes, with the corresponding preimmunsera. After washing plates were incubated with 1:3 diluted sera from five Phl p 2-sensitized grass pollen allergic patients and bound IgE antibodies were detected with alkaline phosphate conjugated monoclonal rat anti-human IgE antibody (Pharmingen, San Diego, Calif.), diluted 1:1000. The percentage inhibition of IgE binding achieved by preincubation with the anti-Phl p 2 mosaic and Phl p 2 was calculated as follows: % inhibition of IgE binding=100−$OD_I/OD_P$×100. $OD_I$ and $OD_P$ represent the extinctions after preincubation with the rabbits immune and preimmune serum, respectively as described by Focke et al., 2001.

The anti-Phl p 2 mosaic antibodies inhibited the binding of grass pollen allergic patients IgE binding to Phl p 2 (20.93% average inhibition) albeit to a lower degree as was achieved by preincubation with antibodies induced by immunization with the rPhl p 2 allergen (54.73% average inhibition).

The results of the immunization studies thus show that antibodies raised against the rPhl p 2 mosaic recognize the Phl p 2 wildtype allergen and inhibit allergic patients IgE recognition of Phl p 2.

The invention claimed is:

1. A hypoallergenic mosaic allergen having the amino acid sequence of SEQ ID NO: 1 and having reduced allergenic activity as compared to Phl p 2 wild type.

2. A medicament comprising the hypoallergenic mosaic allergen of claim 1.

* * * * *